United States Patent [19]
Dougherty

[11] Patent Number: 5,100,624
[45] Date of Patent: Mar. 31, 1992

[54] APPARATUS FOR DETERMINING THE STABILITY OF A PEROXYGEN

[75] Inventor: Edward F. Dougherty, League City, Tex.

[73] Assignee: FMC Corporation, Philadelphia, Pa.

[21] Appl. No.: 532,777

[22] Filed: Jun. 4, 1990

[51] Int. Cl.$^5$ .................... G01N 7/14; G01N 11/06
[52] U.S. Cl. .................... 422/68.1; 422/78; 422/80; 436/34; 436/135; 73/19.04
[58] Field of Search .......... 422/68.1, 78, 80; 436/34, 135, 148, 127; 73/19.04

[56] References Cited

U.S. PATENT DOCUMENTS

| | | | |
|---|---|---|---|
| 2,619,408 | 4/1950 | Mengel | 23/230 |
| 3,150,516 | 9/1961 | Linnenbom et al. | 73/19 |
| 3,400,585 | 7/1965 | Kraus et al. | 73/194 |
| 3,578,404 | 12/1967 | Walles et al. | 23/230 |
| 3,589,172 | 6/1971 | Bowman | 73/25 |
| 3,681,022 | 8/1972 | Kibbel et al. | 23/207.5 |
| 4,050,896 | 9/1977 | Raffel et al. | 23/230 A |
| 4,304,120 | 12/1981 | Myers et al. | 73/19 |
| 4,444,041 | 4/1984 | Zison | 73/19 |
| 4,515,008 | 5/1985 | Matsushita et al. | 73/53 |
| 4,585,622 | 4/1986 | Bowe et al. | 422/50 |
| 4,680,271 | 7/1987 | Williams | 436/55 |

OTHER PUBLICATIONS

Roth et al., "Stability of Pure Hydrogen Peroxide," Ind. & Eng. Chem., 45,10, pp. 2343-2349, Oct. 1953.

Primary Examiner—David L. Lacey
Assistant Examiner—David Redding
Attorney, Agent, or Firm—R. E. Elden; P. C. Baker; R. L. Andersen

[57] ABSTRACT

An apparatus and a method is provided for measuring the rate of flow of gas from a sample of a peroxygen, such as, hydrogen peroxide, thereby indicating the stability of the peroxygen. The invention overcomes the disadvantages of the prior methods which are less precise and have a long time delay.

16 Claims, 2 Drawing Sheets

HYDROGEN PEROXIDE DECOMPOSITION RATE

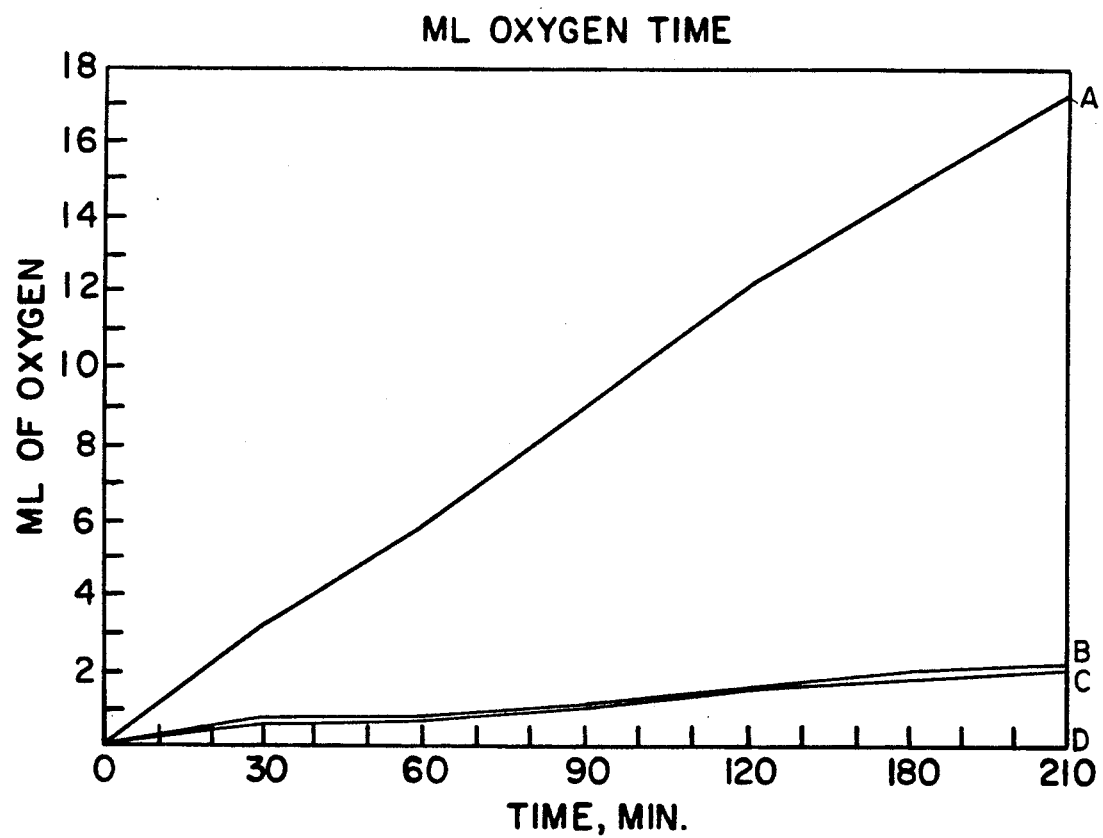

APPARATUS FOR DETERMINING THE STABILITY OF A PEROXYGEN

The invention is an apparatus and a method for determining the stability of a peroxygen by measuring the rate of oxygen gas evolution therefrom.

The determination of the stability of hydrogen peroxide historically has been a problem because it is so stable when pure that years are required to detect a measurable change in concentration when stored at ambient temperatures. On the other hand, in the presence of catalysts the rate of decomposition can become extremely rapid.

Because commercial hydrogen peroxide is so stable its stability is generally determined by an accelerated method, such as, measuring the change in assay of a sample maintained for a standard period of time, 24 hours, at 100° C. as disclosed in U.S. Pat. No. 3,681,022 to Kibbel et al. The method has two disadvantages; the 24 hour time delay, and the lack of both accuracy and precision. The accuracy and precision can be improved by substituting careful gravimetric techniques for volumetric methods, but at the cost of greatly increased analytical time.

Measurement of the oxygen gas evolved during the stability determination was described by Roth et al., "Stability of Pure Hydrogen Peroxide," *Ind. Eng. Chem.*, 45, 2343 (1953). There the oxygen gas evolved was measured in a closed system by use of a modified Warburg manometer. However, the method requires at least several days for each determination plus the time required for the system to reach equilibrium. Even then, 66° C. was the maximum temperature that could be employed. Other disadvantages are that each flask must be individually calibrated because the method is based on measuring the change of pressure of a constant volume of gas and involves calculations to correct for changes in barometric pressure.

The present invention provides an apparatus for determining the stability of a peroxygen comprising:
(a) a sample receiving means adapted to receiving and confining a sample of a peroxygen;
(b) a gas flow sensor;
(c) conduit means adapted to directing gas from sample receiving means to the gas flow sensor;
(d) means for maintaining the peroxygen sample at a predetermined temperature;
(e) timing means;
(f) intelligence processing means;
(g) means to direct output from the gas flow sensor to the intelligence processing means;
(h) means to direct output from the timing means to the intelligence processing means; and
(i) means to record output from the intelligence processing means.

The sample receiving means is essentially a container for receiving and holding the sample to be tested. It must be free from peroxygen decomposition catalysts, it must be substantially inert or nonreactive to the peroxygen solution being evaluated and it must have a capacity to hold sufficient peroxygen, preferably as a solution, to provide meaningful results within a few hours. The sample receiving means may be fabricated from any suitable material such as borosilicate glass, gold, quartz, tantalum, zirconium, aluminum or the like. Preferably the sample receiving means will be a borosilicate glass flask.

One skilled in the art will readily recognize that the capacity of the sample receiving means should be large enough to contain sufficient peroxygen to provide a flow of oxygen gas within the range of sensitivity of the gas flow sensor. It is desirable that the volume of gas in the sample receiving means be sufficiently small to minimize errors caused by slight changes in barometric pressure or temperature fluctuations. The volume should be such that the sample occupies from 1% to 99% of the sample receiving means, desirably from 10% to 90% and preferably 50% to 80%.

Until now the gravimetric methods for determining the stability of peroxygen solutions have been so imprecise that it was necessary that all the samples be maintained at 100° C. for 16 to 24 hours; a shortened time period was not feasible. Even the very precise gas evolution work of Roth et al. could not determine whether or not the decomposition of hydrogen peroxide is a zero order reaction. However, contrary to the presumption of Roth et al. it has been found that the decomposition rate of commercial samples of hydrogen peroxide sufficiently approximates a zero order reaction so that it is possible to extrapolate to 24 hours the decomposition determined after one or two hours. This unexpected finding permits reducing the time of a stability test from 24 hours to 1 hour or even less.

Stability is usually reported as the percent of peroxygen remaining after a standard time. That is, after 24 hours at 100° C.; after 1 year at 30° C.; after 1 year at ambient temperature. However, for the purpose of this invention stability can be reported in any convenient form, such as rate of decomposition (oxygen evolution) per unit time or any other equivalent relationship.

Any gas flow sensor can be employed which is suitable for use with a gas containing oxygen and which generates an output signal which can be directed or transmitted to an intelligence processing means. Desirably, the gas flow sensor will have sufficient precision and accuracy to permit measurement of 0.02 ml of gas per minute or less. That sensitivity will permit extrapolation of a 1 hour determination of a 100 ml or smaller sample of commercial 35% commercial hydrogen peroxide to 24 hours within ±0.1%. An ideal gas flow sensor which is marketed by AED Corporation of Chicago, Illinois, as model DF 4000 gas flow transducer which has sufficient sensitivity to determine the flow of 0.003 ml of oxygen per minute. Clearly, the apparatus can be adapted to measure the stability of any peroxygen concentration from less than 1% by adjusting the sample size according to the sensitivity and range of the gas flow sensor.

Any suitable means may be employed to maintain the samples at the desired temperature. The usual commercial standard for the accelerated stability test at 100° C. is a water bath. However, other means such as a thermostatically-controlled air bath, metal block or the like may be selected to meet the convenience of one skilled in the art. In particular, when small sample receiving means are employed, an aluminum block drilled to receive the sample receiving means is convenient as it eliminates the need of the hood to remove water vapor as is normally required with a 100° C. water bath.

Although timing can be accomplished by an individual manipulating switches and valves by hand when cued by a clock, it is desirable to use some automated timing means, such as a mechanical timer or an electronically programmed timer. Preferably, the timer means is a part of the intelligence processing means, such as a computer or a mechanical recording device as disclosed in U.S. Pat. No. 3,578,404.

The intelligence processing means may optionally merely translate the output from the gas flow sensor and timing means into an output form readable by the operator, such as a graph. Desirably, it will combine the gas flow sensor output and timing means output to calculate the quantity of oxygen evolved per unit time, or the equivalent such as peroxygen decomposition, peroxygen stability or the like. Intelligence processing means may indicate or record its output by meters, screens, digital displays, graphical output, electromagnetic signals, printing or the like or as a combination thereof. The intelligence processing means may present the output graphically, as numerical data or both. Optionally, the intelligence processing means may store the data, perform statistical calculations and the like. An intelligence processing means may be a recording chart device as disclosed in U.S. Pat. No. 3,578,404 or a computer with suitable software. For example, in the subsequent examples a desk top computer was employed which processed the gas flow sensor data and timing means data with Labtech Notebook ®, and calculations performed using LOTUS 1-2-3 ® software.

The means to transmit output from gas flow transmitter and/or timing means to intelligence processing means may be varied and can be selected by one skilled in the art without undue experimentation. When the timing means is a synchronous motor and the intelligence processing means is a mechanical recording device, the means is usually a set of gears and cams which mechanically direct or transfer the mechanical output from the timing means while electronic timing means may direct or transfer its output as electronic signals or pulses through conductors, or the mother board if the intelligence processing means is a computer. Output from one or more gas flow sensors may be directed to the intelligence processing means as electronic, electrical, optical, pneumatic, magnetic, electromagnetic, hydraulic, or mechanical methods, or may be transmitted by a combination of the same. Preferably, when the gas flow sensor output is electronic in nature and the intelligence processing means is a computer equipped with software, the means to direct the output from one or more gas flow sensors are generally composed of wires or electronic cables, and if multiple sensors are employed, by a multiplexer.

The process for determining the stability of a sample of a peroxygen by the present invention is a series of steps comprising:
a. introducing a sample of a peroxygen into a sample receiving means,
b. maintaining the sample in the sample receiving means at a constant temperature,
c. directing gas from the sample receiving means to a gas flow sensor,
d. measuring the rate of flow of gas from the sample receiving means,
e. directing output from the flow measuring device to an intelligence processing means,
f. calculating the stability of the peroxygen solution,
g. recording the stability,
h. repeating steps (b) through (g) for a sufficient number of replications until at least two consecutive stabilities indicate equilibrium has been reached and the recorded stabilities are within limits of the experimental error, and
i. displaying the stability determined in step (h).

One skilled in the art will recognize it is critical to maintain the peroxygen at a constant temperature, because of the known effects a change of temperature has on decomposition rate, gas volume, gas solubility and the like. Conventionally, the temperature is maintained at about 100° C., but any meaningful or convenient temperature below the boiling point of the sample could be employed.

It is desirable to employ a condenser to exclude vapor from the gas flow sensor, and also to prevent evaporation from the sample to substantially change the volume thereof, and to minimize errors from changes in ambient temperature.

It is preferable that the gas from the container be free to flow from the gas flow sensor to a constant pressure reservoir, such as the atmosphere outside the apparatus, thereby eliminating the need to measure the pressure and/or volume of gas in the container. Generally, it is unnecessary to account for any change of atmospheric pressure because of the short time required for a determination by the process of the invention.

As the process is based on measuring a small flow of gas evolved by the decomposition of a sample of a peroxygen, it is not critical to have a very precise assay of the sample or of the quantity in the container. It is only necessary that the assay and sample size be known within about ±5% to determine the stability within 0.5% under normal conditions. Clearly, any peroxygen solution may be employed, such as hydrogen peroxide, peracetic acid, solutions of sodium perborate, sodium carbonate perhydrate and solutions of formulations or mixtures containing a peroxygen, or even a solid peroxygen, such as sodium persulfate, calcium peroxide and the like.

The best mode for practicing the invention will be clear to one skilled in the art from the following nonlimiting examples employing a prototype apparatus.

BRIEF DESCRIPTION OF DRAWINGS

FIG. 3 is a computer print-out of the results of example 4 as determined by the invention.

Figure 1:
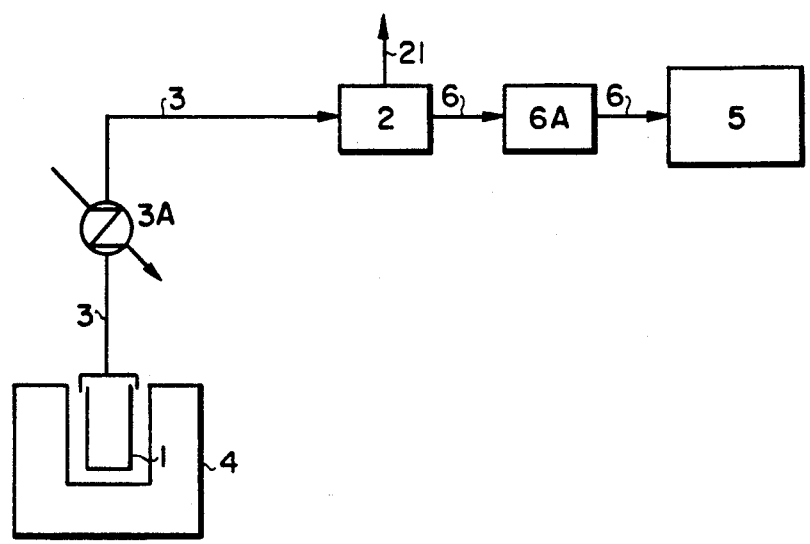
FIG. 1 is a block diagram showing a prototype apparatus.

Sample receiving means 1 is maintained at a predetermined temperature by being inserted in a cavity of temperature maintaining means 4, an aluminum block maintained at a predetermined temperature. Oxygen from sample receiving means 1 is directed by conduit means 3 to gas flow sensor 2. Water condenser 3A is preferably employed as part of conduit means 3. Gas is vented to the atmosphere through conduit 21. Output from gas flow sensor 2 is directed by electronic cable system 6 to intelligence processing means 5. Optionally included as part of electronic cable system 6 is a multiplexer 6A which provides ability to connect a plurality of gas flow sensors with associate sample receiving means to intelligence processing means 5. Intelligence processing means is a desk top computer system with software containing (a) built in timing means (not shown) connected internally by mother board means to be utilized by the software, and (b) means to record output selected from the group output screen, printer and magnetic data storage.

In the following examples, aqueous peroxide sample (hydrogen peroxide) is confined in sample receiving means 1 which is maintained at about 100° C. (100°

C.±1% C.), partially decomposing said sample to form ½ mole of oxygen gas per mole of peroxygen decomposed, causing gas from sample receiving means to be directed through optional water condenser 3A to gas flow sensor means 2 where it is vented to the atmosphere through conduit 21. Output from gas flow sensor 2 is directed by electronic wiring 6 and multiplexer 6A to intelligence processing computer 5 utilizing software and timer adapted to provide as output graphically and in digital form the volume of oxygen evolved and the 24 hour stability extrapolated therefrom. Initially, the measured rate of flow will vary, but will gradually approach a constant value indicating that the system has attained equilibrium. After equilibrium has been attained successive determination of stability or gas flow rate are normally constant within the limits of experimental error. The magnitude of any deviations generally depend on sample size, temperature control and the like.

EXAMPLE 1

The rate of oxygen evolution from a sample of an aqueous peroxygen was determined using a calibrated gas burette over water. A 2 ml sample of impure 75% hydrogen peroxide having a very poor stability was maintained at 100° C. during the test. No attempt was made to maintain the collected gas at a constant temperature, correct for barometric pressure, or the solubility of oxygen in hydrogen peroxide. The results are presented as Table I.

Surprisingly, the decomposition rate was essentially constant throughout the experiment indicating a zero order decomposition reaction. During more than two days the assay of the sample fell from 75% to about 26%. This zero order decomposition is unexpected according to Roth et al. (supra).

EXAMPLE 2

The 100° C. stability of six commercial samples of 35% technical grade hydrogen peroxide were determined both by the 24 hour gravimetric method and by using a prototype apparatus of FIG. 1 for 3 hours. The results are presented as Table II.

EXAMPLE 3

Figure 2:
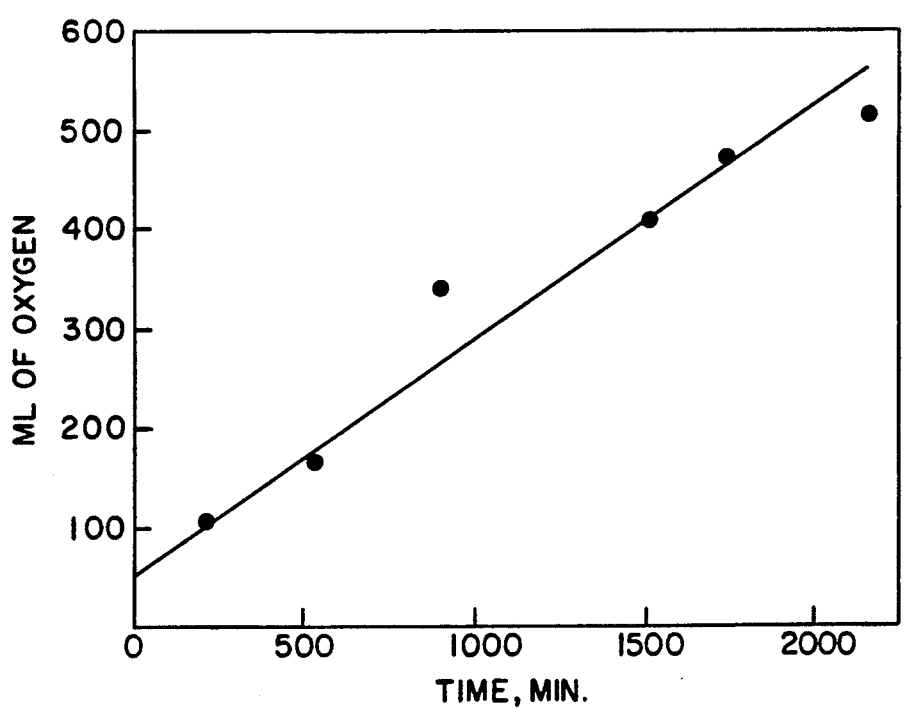
FIG. 2 shows the decomposition rate of a hydrogen peroxide sample as measured by the invention.

A sample of unstabilized hydrogen peroxide with a poor stability was evaluated consisting of prototype apparatus of FIG. 1 in which an IBM computer using LOTUS 1-2-3 software acted as the intelligence processing means. The results are presented as FIG. 2, the computer printout.

EXAMPLE 4

Samples of 35% hydrogen peroxide unstabilized (A), and stabilized with two different formulations (B and C) were simultaneously run in the prototype apparatus of FIG. 3. Water was employed as sample D. The results are presented as the computer printout, FIG. 3.

TABLE I

| OXYGEN EVOLUTION FROM 75% HYDROGEN PEROXIDE | | |
| --- | --- | --- |
| Minutes | ml | ml/min. |
| 0 | 0 | |
| 100 | 25 | .25 |
| 350 | 60 | .171 |
| 435 | 80 | .184 |
| 590 | 110 | .186 |
| 755 | 155 | .205 |

TABLE I-continued

| OXYGEN EVOLUTION FROM 75% HYDROGEN PEROXIDE | | |
| --- | --- | --- |
| Minutes | ml | ml/min. |
| 840 | 190 | .226 |
| 1,020 | 260 | .254 |
| 1,200 | 300 | .250 |
| 1,380 | 350 | .254 |
| 1,690 | 425 | .250 |
| 2,770 | 580 | .209 |
| 3,310 | 600 | .181 |

TABLE II

24 HOUR STABILITY COMPARISON, 35% HYDROGEN PEROXIDE GRAVIMETRIC vs. GAS FLOW

| | % Stability | |
| --- | --- | --- |
| Sample | Gravimetric 24 hour | Gas Flow 3 hour |
| 1 | 92.4 | 92.7 |
| 2 | 87.8 | 88.8 |
| 3 | 91.7 | 91.6 |
| 4 | 96.0 | 95.1 |
| 5 | 93.1 | 92.7 |
| 6 | 94.0 | 93.1 |

I claim:
1. Apparatus for determining the stability of a peroxygen consisting essentially of:
   (a) a sample receiving means constructed so as to receive and confine a sample of a peroxygen;
   (b) a gas flow sensor;
   (c) conduit means for directing gas from said sample receiving means to the gas flow sensor;
   (d) means for maintaining the peroxygen sample in the sample receiving means at a predetermined temperature below the boiling point of the sample of peroxygen;
   (e) timing means;
   (f) intelligence processing means;
   (g) means to direct output from at least one gas flow sensor to the intelligence processing means;
   (h) means to direct output from the timing means to the intelligence processing means, whereby the processing means calculates a zero order stability value of the peroxygen sample; and
   (i) means to record the zero order stability value output from the intelligence processing means.

2. The apparatus of claim 1 wherein the gas flow sensor is a mass flow transducer.

3. The apparatus of claim 1 wherein the means for maintaining the temperature is constructed so as to maintain a predetermined temperature of 100° C.

4. The apparatus of claim 2 wherein the means for maintaining the temperature is constructed so as to maintain a predetermined temperature of 100° C.

5. The apparatus of claim 1 wherein the intelligence processing means is a computer.

6. The apparatus of claim 2 wherein the intelligence processing means is a computer.

7. The apparatus of claim 3 wherein the intelligence processing means is a computer.

8. The apparatus of claim 4 wherein the intelligence processing means is a computer.

9. The apparatus of claim 1 wherein the gas flow sensor is a mass flow transducer with sufficient sensitivity to measure a flow of at least 0.02 ml of gas per minute.

10. The apparatus of claim 2 wherein the gas flow sensor is a mass flow transducer with sufficient sensitivity to measure a flow of at least 0.02 ml of gas per minute.

11. The apparatus of claim 3 wherein the gas flow sensor is a mass flow transducer with sufficient sensitivity to measure a flow of at least 0.02 ml of gas per minute.

12. The apparatus of claim 4 wherein the gas flow sensor is a mass flow transducer with sufficient sensitivity to measure a flow of at least 0.02 ml of gas per minute.

13. The apparatus of claim 5 wherein the gas flow sensor is a mass flow transducer with sufficient sensitivity to measure a flow of at least 0.02 ml of gas per minute.

14. The apparatus of claim 6 wherein the gas flow sensor is a mass flow transducer with sufficient sensitivity to measure a flow of at least 0.02 ml of gas per minute.

15. The apparatus of claim 7 wherein the gas flow sensor is a mass flow transducer with sufficient sensitivity to measure a flow of at least 0.02 ml of gas per minute.

16. The apparatus of claim 8 wherein the gas flow sensor is a mass flow transducer with sufficient sensitivity to measure a flow of at least 0.02 ml of gas per minute.

* * * * *